United States Patent [19]

Vedamuthu

[11] Patent Number: 5,066,588

[45] Date of Patent: Nov. 19, 1991

[54] *STREPTOCOCCUS LACTIS* CONTAINING PLASMIDS ENCODING FOR MUCOIDNESS AND METHOD FOR IDENTIFYING SUCH STRAINS

[75] Inventor: Ebenezer R. Vedamuthu, Bradenton, Fla.

[73] Assignee: Microlife Technics, Inc., Sarasota, Fla.

[21] Appl. No.: 189,388

[22] Filed: May 2, 1988

Related U.S. Application Data

[63] Continuation-in-part of Ser. No. 786,631, Oct. 11, 1985, Pat. No. 4,918,014.

[51] Int. Cl.$^5$ .................. C12N 1/21; C12N 15/10
[52] U.S. Cl. .................. 435/172.3; 435/69.1; 435/71.1; 435/91; 435/170; 435/172.1; 435/252.3; 435/320.1; 435/885; 536/27; 935/6; 935/9; 935/22; 935/29; 935/59; 935/72
[58] Field of Search .................. 435/69.1, 71.1, 91, 435/170, 172.1, 172.3, 252.3, 320.1, 885; 536/27; 935/6, 9, 22, 29, 59, 72

[56] References Cited

PUBLICATIONS

Hammer, B. W., Iowa Agr. Expt. Sta. Research Bul. 74:260-270 (1923).
Foster, E. M. et al., Dairy Microbiology, pp. 14-15, 48 and 332 (1957).
Rasic, J. L. et al., Yoghurt-Scientific Grounds, Technology, Manufacture and Preparations, p. 194 (1978).
Bottazzi, V., Biotechnology, vol. 5, p. 328, 345-346 (1983).
Macura, D. et al., J. Dairy Sci. 67:735-744 (1984).
Saxelin, M. et al., Canadian J. Microbiol. 25:1182-1187 (1979).
Forsen, R., Finnish J. Dairy Sci. 26:1-76 (1966).
Brooker, B. E., J. Dairy Research 43:283-290 (1976).
Sozzi et al., Milchwissenschaft 33: 349-352 (1978).
McKay, L. L., J. Microbiol. 49:259-274 (1983).
McKay et al., Applied Environmental Microbiology 47:68-74 (1984).
Klaenhammer, T. R., Advances in Applied Microbiology 30:1-29 (1984).
Anderson, D. G. et al., Appl. Environ. Microbiol. 46:549-552 (1983).
Gonzalez, C. F., et al., Appl. Environ. Microbiol. 46:81-89 (1983).
Southern, E. M., J. Mol. Biol. 98:503-517 (1975).
Silhavy, T. J. et al., Ezperiments with Gene Fusions, pp. 89-96, 104, 186-195 and 218 Cold Spring Harbor Laboratory, Cold Spring Harbor, N.Y. (1984).
Vedamuthu, E. R. et al., Appl. Environ. Microbiol, 51:677-682 (1986).
Walsh, P. M., and L. L. McKay, J. Bacteriol. 146:937-944 (1981).

*Primary Examiner*—Richard A. Schwartz
*Assistant Examiner*—Richard C. Peet
*Attorney, Agent, or Firm*—Ian C. McLeod

[57] ABSTRACT

A lactose-fermenting (Lac+), mucoid (Muc+) *Streptococcus lactis* transconjugant designated ML-3/2.230 was obtained by conjugative co-transfer of Lac+ Muc+ phenotypes from Lac+ Muc+ *Streptococcus cremoris* MS to lactose-negative (Lac+), non-mucoid *S. lactis* ML-3/2.2. Curing studies on the transconjugant ML-3/2.230 showed that Muc+ phenotype in the strain was encoded on two plasmids, pSRQ2203 and pSRQ2204. DNA hydridization experiments also indicated the involvement of two plasmids in the expression of the mucoid phenotype. Plasmid pSRQ2203 also contained genetic information for lactose utilization (Lac+).

11 Claims, 2 Drawing Sheets

STREPTOCOCCUS LACTIS CONTAINING PLASMIDS ENCODING FOR MUCOIDNESS AND METHOD FOR IDENTIFYING SUCH STRAINS

CROSS-REFERENCE TO RELATED APPLICATION

This application is a continuation-in-part of U.S. application Ser. No. 786,631 filed Oct. 11, 1985 now U.S. Pat. No. 4,918,014.

BACKGROUND OF THE INVENTION

(1) Field of the Invention

The present invention relates to improved *Streptococcus lactis* containing two plasmids which together encode for mucoidness. Further, the present invention relates to a method wherein plasmid DNA known to encode for mucoidness is used as a probe to determine whether or not the *Streptococcus lactis* encode for mucoidness.

(2) Prior Art

The occurrence of lactic streptococci that produce a mucoid, ropy texture in milk is well documented (Hammer, B. W., Iowa Agr. Expt. Sta. Research Bul. 74:260-270 (1923)). Such ropy lactic streptococci are used in Scandinavian fermented milks called taette (Foster, E. M., et al., Dairy Microbiology, p. 14-15, 48 and 332, (1957); Rasic, J. L. et al., Yoghurt-Scientific grounds, technology, manufacture and preparations, p. 194 (1978)), Swedish lang mjolk (Bottazzi, V., Biotechnology, Vol. 5, p. 328, 345-346 (1983); Macura, D., et al., J. Dairy Sci. 67:735-744 (1984)) and Finnish villii (Saxelin, M., et al., Canadian J. Microbiol. 25:1182-1187 (1979)). Forsen, R., Finnish J. Dairy Sci. 26:1 (1966) isolated mucoid strains of all three lactic streptococci, namely, *Streptococcus cremoris, Streptococcus lactis* and *Streptococcus lactis* subsp. *diacetylactis*, from Finnish villii.

The instability of mucoid characteristic in lactic streptococci has been observed by several investigators (Foster, E. M., et al., Dairy Microbiology. p. 14-15, 48 and 332 (1957); Hammer, B. W., Iowa Agr. Expt. Sta. Research Bul. 74: 260-270 (1923); and Macura, D., et al. J. Dairy Sci. 67: 735-744 (1984)). Foster et al reported that mucoid lactic streptococci gained or lost the slime-producing property "capriciously". Macura and Townsley found that ropy lactic streptococci lost the mucoid property after 10 or 12 serial transfers; some strains became non-mucoid even after six transfers. Brooker (Brooker, B. E., J. Dairy Research 43:283-290 (1976)) working with a pure milk culture of a ropy *S. cremoris* strain observed considerable variations in the proportion of cells producing extracellular capsular material. Traditionally, in the production of Scandinavian ropy milks, low temperature incubation between 13° C. to 18° C. is preferred, because incubation at temperatures higher than 27° C. to 30° C. resulted in considerable reduction or loss of desirable high viscosity and mucoidness (Bottazzi, V., Other Fermented Dairy Products. p. 328, 345-346. In: G. Reed (ed.), Biotechnology-Vol. 5, Food and Feed Production with Microorganisms. Verlag Chemie, Weinheim, Federal Republic of Germany (1983); and Macura, D., et al. J. Dairy Sci. 67: 735-744(1984)). It had been suggested by early prior art that the mucoidness might protect the lactic Streptococcus against bacteriophage; however, this was shown to be wrong. Sozziet al., Milchwissenschaft 33, 349-352 (1978).

The association of several metabolic functions in lactic streptococci with plasmid DNA is now well recognized (McKay, L. L., J. Microbiol. 49:259-274 (1983)). On the basis of the observed instability of ropy characteristic in lactic streptococci, Macura and Townsley (Macura, D., et al., J. Dairy Sci. 67:735-744 (1984)) and McKay suggested that plasmid DNA may be involved in the expression of mucoid phenotype (Muc+).

A problem in the prior art is to be able to detect and produce phage resistant strains of Streptococcus which are members of group N, particularly *Streptococcus lactis*. It would be highly desirable to be able to impart phage resistance to strains of Streptococcus which are phage sensitive since these bacteria are very important in commercial fermentations for producing fermented milk products. McKay et al., Applied Environmental Microbiology, 47; 68-74 (1984) describes limited phage resistance which is plasmid associated. Klaenhammer, T. R., Advances in Applied Microbiology 30, 1-29 (1984) at page 22 discusses plasmid encoded phage resistance. Phage resistance has not been associated with a 18.5 Mdal plasmid in *Streptococcus cremoris* encoding for mucoidness. Further, *Streptococcus cremoris* NRRL-B-15995 was obtained as a single colony isolated from a phage resistant strain but is a slow acid producer and thus is not a useful strain for milk fermentations.

GENERAL DESCRIPTION

The present invention relates to a *Streptococcus lactis* containing two plasmids derived from a single plasmid in *Streptococcus cremoris* NRRL-B-15995 by conjugal transfer which both encode for mucoidness. Particular strains are *Streptococcus lactis* NRRL-B-18337 and NRRL-B-18338 which contain the plasmids.

Further the present invention relates to a method for producing a *Streptococcus lactis* containing at least two plasmids which together encode for mucoidness which comprises: conjugating a *Streptococcus lactis* which does not produce mucoidness with a mucoid *S. cremoris* strain, which contains a plasmid, preferably pSRQ2202 encoding for mucoidness; and isolating a strain containing two recombinant plasmids both of which are necessary to encode for mucoidness.

Further the present invention relates to labeled plasmid DNA derived from pSRQ2202 as originally carried in *Streptococcus cremoris* NRRL-B-15995 by nick translation which selectively binds to unknown DNA bound to a surface to determine whether the unknown DNA is homologous to pSRQ2202.

Finally the present invention relates to a method for detecting the presence of unknown plasmid DNA which can encode for mucoidness which comprises: reacting unknown DNA from a Streptococcus with labeled DNA derived from a plasmid encoding for mucoidness in a Streptococcus by nick translation and labeling to produce the labeled DNA to determine whether the unknown DNA is homologous to the labeled DNA encoding for mucoidness is present by binding of the labeled DNA to the unknown DNA.

The bacterial cells can be prepared for use in foods and the like as a concentrate having a pH between about 4 and 8 and containing at least about $1 \times 10^7$ cells per gram up to about 1015 cells per gram, usually between about $1 \times 10^9$ and $10^{12}$ cells per gram. The concentrates can be frozen with or without a freezing stabilizing agent such as monosodium glutamate, malt extract, non-fat dry milk, alkali metal glycerophosphate, glutamic acid, cystine, glycerol, or dextran or the like and then thawed for use or the concentrates can be lyophilized or dried by other means to a powder as is well known to those skilled in the art. The bacterial cells are generally used in a range between about $10^5$ to $10^9$ cells per ml of milk to be fermented, depending upon the product to be produced. All of this is very well known to those skilled in the art. U.S. Pat. No. 3,420,742 describes various preservation methods.

U.S. Pat. No. 4,382,097 to one of the inventors herein describes mixed cultures including mucoid substance producing (Muc+) strains. Mucoid substance producing strains of the present invention can be used in the preparation of these mixed cultures with good results.

*Streptococcus cremoris* NRRL-B-15995, also known as "MS", has been deposited under the Budapest Treaty with the Northern Regional Research Laboratory in Peoria, Illinois similarly *Streptococcus lactis* NRRL-B-18337 and NRRL-B-18338 have been deposited with this laboratory under the Budapest Treaty.

In Ser. No. 786,631, now U.S. Pat. No. 4,918,014, a two-step process is described by which lactose fermenting ability (Lac+) coded by pSRQ2201, and the ability to produce a mucoid coagulum in milk (Muc+) coded by pSRQ2202 were conjugatively transferred from a mucoid *S. cremoris* NRRL-B-15995 strain to a Lac− (incapable of lactose fermentation), non-mucoid *S. lactis* strain designated ML-3/2.2. In the first step, transfer of pSRQ2201 yielded the Lac+, non-mucoid transconjugant *S. lactis* ML-3/2.201. The Muc-plasmid, pSRQ2202 was then transferred to *S. lactis* ML-3/2.201 to obtain Lac+ Muc+ transconjugant *S. lactis* ML-3/2.202. The plasmid complement of *S. lactis* ML-3/2.202 contained both pSRQ2201 and pSRQ2202. Only pSRQ2202, a 18.5 Mdal plasmid, encoded for mucoidness.

In the present invention, a one-step co-transfer of both Lac+ and Muc+ phenotypes from Lac+ Muc+ *S. cremoris* MS to Lac−, non-mucoid *S. lactis* ML-3/2.2 was achieved. This produced *S. lactis* NRRL-B-18337 (ML-3/2.230), a transconjugant obtained through such co-transfer of Lac+ and Muc+ phenotypes. The two plasmids in the transconjugant strain were both involved with the Muc+ phenotype. Also, using the Muc+ plasmid, pSRQ2202, as a radiolabelled DNA hybridization probe, two plasmids in the transconjugant displayed positive hybridization signals demonstrating recombinational events during conjugation.

Bacterial strains used in this study are listed in Table 1.

TABLE 1

| Streptococcus strain[a] | Relevant Phenotype[b] | Relevant Plasmid(s) | Comments (Reference)[c] |
|---|---|---|---|
| S. cremoris MS | Lac+, Muc+ | pSRQ2201 (75.8 Mdal) pSRQ2202 (18.5 Mdal) | NRRL-B-15995 |
| S. lactis ML-3/2.2 | Sm$^r$, Fus$^r$ | — | Lac-cured derivative of S. lactis ML-3 |
| ML-3/2.202 | Sm$^r$, Fus$^r$, Lac+ Muc+ | pSRQ2201 pSRQ2202 | S. cremoris MS04 × S. lactis ML-3/2.201 transconjugant |
| ML-3.2.230 | Sm$^r$, Fus$^r$, Lac+, Muc+ | pSRQ2203 (60.0 Mdal) pSRQ2204 (31.0 Mdal) | S. cremoris MS + S. lactis ML-3/2.2 transconjugant; NRRL-B-18337 |
| ML-3/2.231 | Sm$^r$, Fus$^r$, Lac− Muc− | — | Cured derivative of ML-3/2.230; |
| ML-3/2.232 | Sm$^r$, Fus$^r$, Lac+, Muc− | pSRQ2203 | Cured derivative of ML-3/2.230; |
| ML-3/2.233 | Sm$^r$, Fus$^r$, Lac− Muc+ | pSRQ2204 pSRQ2205 (41.0 Mdal) | Cured derivative of ML-3/2.230; NRRL-B-18338 |
| ML-3/2.234 | Sm$^r$, Fus$^r$, Lac− Muc− | pSRQ2204 | Cured derivative of ML-3/2.230; |
| ML-3/2.235 | Sm$^r$, Fus$^r$, Lac− Muc− | pSRQ2204 | Cured derivative of ML-3/2.233; |
| ML-3.2.236 | Sm$^r$, Fus$^r$, Lac− | pSRQ2205 | Cured derivative of |

TABLE 1-continued

| Streptococcus strain[a] | Relevant Phenotype[b] | Relevant Plasmid(s) | Comments (Reference)[c] |
|---|---|---|---|
| | Muc$^-$ | | ML-3/2.233; |

[a]Viscosity values in centipoises for mucoid strain cultures: S. cremoris MS = 1175; S. lactis ML-3/2.202 = 800; S. lactis ML-3/2.230 = 1350; S. lactis ML-3/2.233 = 1100.
Viscosity values for all non-mucoid cultures were <150 centipoises.
[b]Lac$^+$ — Lactose fermented;
Lac$^-$ — Negative for lactose fermentation;
Muc$^+$ — Mucoid;
Muc$^-$ — Non-mucoid;
Sm$^r$ — Resistant to streptomycin (1000 μg/ml);
Fus$^r$ — Resistant to fusidic acid (20 g/ml);
Rif$^r$ — Resistant to Rifampin (200 μg/ml).
[c]Lac-cured = Cured of lactose fermenting ability.

Cultures were purified and propagated in media and under conditions in Ser. No. 786,631 now U.S. Pat. No. 4,918,014. Procedures used for curing, mating and characterization of transconjugants including qualitative and quantitative determination of mucoidness were done as previously described in Ser. No. 786,631. The procedures are also described in Applied Environmental Microbiology 51, 677–682 (1986).

Procedures described by Anderson and McKay (Anderson, D. G., and L. L. McKay., Appl. Environ. Microbiol. 46:549–552 (1983)) and Gonzalez and Kunka (Gonzalez, C. F., and B. S. Kunka, Appl. Environ Microbiol. 46:81–89 (1983)) were used for cell lysis. Examination of plasmid DNA by agarose slab gel electrophoresis was done according to the procedure described by Gonzalez and Kunka (Gonzalez, C. F., and B. S. Kunka, Appl. Environ Microbiol. 46:81–89 (1983)).

Plasmid DNA separated electrophoretically on agarose gel was transferred to nitrocellulose film according to the procedure of Southern (Southern, E. M., J. Mol. Biol. 98:503–517 (1975)). DNA probes were prepared by nick translation (New England Nuclear Corp., Boston, Mass.). Hybridization procedures were as described by Silhavy et al (Silhavy, T. J., M. L. Berman, and L. M. Enquist., Experiments with gene fusions, pp. 89–96, 104, 186–195, and 218. Cold Spring Harbor Laboratory, Cold Spring Harbor, N.Y. (1984)). Washed and dried filters were autoradiographed with Kodak X-Omat film and Lightning-Plus screens (E. I. duPont de Nemours & Co., Inc., Wilmington, Del.) at −70° C.

The co-transfer of Lac$^+$ Muc$^+$ phenotypes from S. cremoris MS (Lac$^+$ Muc$^+$; donor) to S. lactis ML-3/2 2 (Lac$^-$, non-mucoid; recipient) occurred at a frequency of $1.3 \times 10^{-9}$. Unlike the previously described Lac$^+$ Muc$^+$ S. lactis transconjugant ML-3/2 202 in Ser. No. 786,631, now U.S. Pat. No. 4,918,014 transconjugant S. lactis ML-3/2 230 obtained by co-transfer of Lac$^+$ Muc$^+$ phenotypes in this study lacked both pSRQ2201 and pSRQ2202 Instead, S. lactis ML-3/2.230 showed the presence of two new plasmids, designated pSRQ2203 and pSRQ2204 (Table 1 and FIG. 1, lane A). Through a series of curing experiments, it was possible to associate the expression of Lac$^+$ and Muc$^+$ phenotypes in S. lactis ML-3/2.230 with pSRQ2203 and pSRQ2204.

Figure 1:
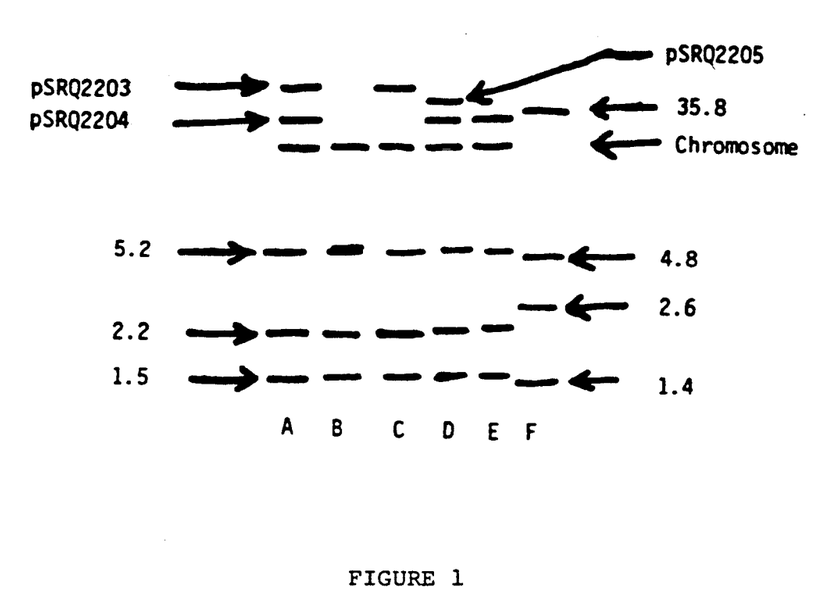
FIG. 1 is a drawing of an agarose gel electrophoresis of plasmid DNA from *S. lactis* transconjugant ML-3/2.230 and its cured derivatives along with reference plasmid DNA for molecular sizing from *E. coli* V517. A=ML−3/2.230(Lac+ Muc+); B=ML−3/2.231 (Lac− Muc−); C=ML−3/2.232(Lac+ Muc−); D=ML−3/2.233(Lac− Muc+); E=ML−3/2.234- (Lac− Muc−); F=*E. coli* V517. The bottom three numbers on the left refer to plasmid sizes in the bacterial strains examined. The bottom three numbers on the right refer to molecular sizes of reference plasmid DNA from *E. coli* V517.

FIG. 1 also shows the results of the curing experiments. Lane A in FIG. 1 shows the presence of 60.0 M Da plasmid pSRQ2203, and 31.0 M Da plasmid pSRQ2204 in the Lac$^+$ Muc$^+$ transconjugant S. lactis ML-3/2.230. Lane B in the same Figure shows the plasmid profile of cured derivative ML-3/2.231, which was non-mucoid (Muc$^-$) and Lac$^-$. In this strains both pSRQ2203 and pSRQ2204 were absent. Derivative ML-3/2.232, which was Lac$^+$ Muc$^-$ lacked only pSRQ2204 (lane C). S. lactis ML-3/2.234, a Lac$^-$ Muc$^-$ derivative possessed pSRQ2204 but did not contain pSRQ2203 (lane E). Analysis of the plasmid contents and the corresponding phenotypes expressed by the parent transconjugant ML-3/2.230 its cured derivatives ML-3/2.231, ML-3/2.232 and ML-3/2.234 indicated that pSRQ2203 coded for Lac$^+$ phenotype because in the absence of pSRQ2203 (as in ML-3/2.231 and ML-3/2.234) the strains were Lac$^-$.

There was no single plasmid species that correlated to the Muc$^+$ phenotype. In the Lac$^+$ Muc$^-$ derivative ML-3/2.232, pSRQ2204 was absent (lane C), but ML-3/2.234 which possessed pSRQ2204 (lane E) was also non-mucoid. This suggested the expression of Muc$^+$ phenotype required the presence of both pSRQ2203 and 2204 as in the parent strain ML-3/2.230.

Further evidence to show that two plasmids are involved in the expression of Muc$^+$ phenotype in ML-3/2.230 was obtained from the Lac-cured Muc$^+$ derivative ML-3/2.233. Isolation of the Lac-cured, Muc$^+$ derivative was difficult and was achieved by a different procedure. High, temperature incubation as described in Ser. No. 786,631 now U.S. Pat. No. 4,918,014. when used for deriving the other variants of ML-3/2.230 always resulted in the simultaneous loss of Lac$^+$ Muc$^+$ phenotypes. To obtain the Lac-cured, Muc$^+$ derivative, ML-3/2.233, the Lac$^+$ Muc$^+$ transconjugant ML-3/2.230 was successively transferred 10 times in whey glucose both with incubation at 24° C. for 16 hours between transfers. At the end of 10th propagation, the culture was plated at $1 \times 10^{-6}$ dilution in triplicate on BML agar. Out of 280 colonies presumed to be Lac-negative, 40 were confirmed to be Lac-negative by replicate plating on BML agar. Of the 40 confirmed Lac-negative isolates, only one retained the Muc$^+$ phenotype. The exact identity of the Lac$^-$ Muc$^+$ derivative, ML-3/2.233 was confirmed by testing the strain for lysis when challenged by phage 643, which was virulent for the parent transconjugant ML-3/2.230 and the non-mucoid strain ML-3/2.2 (Table 1). In S. lactis ML-3/2.233, pSRQ2204 was intact but pSRQ2203 was absent. The strain, however, possessed a 41.0 M Da plasmid designated pSRQ2205 (Table 1, FIG. 1, lane D). Plasmid pSRQ2205 observed in ML-3/2 233 was probably formed by the deletion of a portion of pSRQ2203 that was necessary for the expression of lactose utilization. The complementary information for Muc$^+$ phenotype in pSRQ2203 was, however, conserved in pSRQ2205 and hence ML-3/2.233 expressed the Lac$^-$ Muc$^+$ phenotype. Additional curing experiments on S. lactis ML-3/2.233 confirmed that expression of Muc$^+$ phenotype in this strain required the presence of both pSRQ2204 and PSRQ2205. When either pSRQ2204 or PSRQ2205 were eliminated from S. lactis ML3/2.233, by high temperature incubation at 41° C. (Vedamuthu, E. R., and J. M. Neville., Appl. Environ. Microbiol. 51:677-682 (1986)) the resultant derivatives were non-mucoid.

Figure 2:
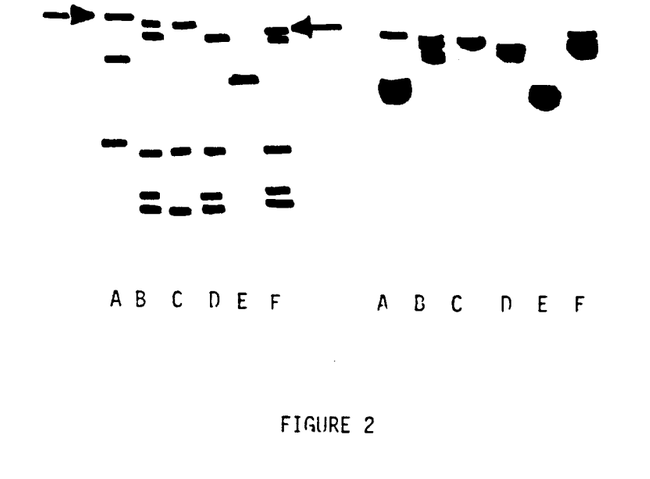
FIG. 2 is a drawing of autoradiograms of plasmid DNA probed with purified Muc-plasmid pSRQ2202. Left: Plasmid DNA separated by agarose gel electrophoresis A. *S. lactis* 4/4.201; B. *S. lactis* ML-3/2.230, C. *S. lactis* ML-3/2.232; D. *S. lactis* ML-3/2.234, E. Purified pSRQ2202; F. *S. lactis* ML-3/2.233. Right: Autoradiograms of corresponding DNA shown in the left panel. Arrow on the left shows the Lac-plasmid pSRQ2201 and arrow on the right indicates the position of pSRQ2205.

FIG. 2 shows the autoradiograms of plasmid DNA from malty S. lactis transconjugant 4/4.201, which harbored both Lac- and Muc-plasmids pSRQ2201 and pSRQ2202, respectively, S. lactis strains ML-3/2.230, ML-3/2.232, ML-3/2.234 and ML-3/2.233 probed with purified Muc-plasmid, pSRQ2202. There was DNA hybridization between the pSRQ2202 probe (lane E) and pSRQ2201 and pSRQ2202 in malty S. lactis 4/4.201 (lane A) and plasmids pSRQ2203, pSRQ2204 (lanes B, C, and D) and pSRQ2205 (lane F). The hybridization found between the pSRQ2202 probe and the Lac-plasmid pSRQ2201 in the malty strain (lane A) suggests that recombinational events between these two plasmids could possibly occur during the conjugal transfer Examination of plasmid profiles and phenotypic characterizations of S. lactis ML-3/2.230, and its derivatives shown in FIG. 1 along with those of the previously described Lac+ Muc+ transconjugant S. lactis ML-3/2 202 suggested that during the co-transfer of Lac+ and Muc+ phenotypes from S. cremoris MS to S. lactis ML-3/2.2, recombinational events had occurred between the 75.8 M Da Lac-plasmid and the 18.5 M Da Muc-plasmid. In the transconjugant S. lactis ML-3/2.230, the recombinational events had resulted in the formation of two new plasmids pSRQ2203 (60.0M Da) and pSRQ2204 (31.0 M Da). Results presented in FIG. 2 show that because of homology between pSRQ2201 and pSRQ2202, such recombinational events have occurred. Formation of new recombinant plasmids during conjugative plasmid transfer among lactic streptococci has been reported by earlier investigators (Walsh, P. M., and L. L. McKay, J. Bacteriol. 146-937-944 (1981)), but not anything related to mucoidness.

EXAMPLE 1

Mucoid, lactose fermenting *Streptococcus cremoris* NRRL-B-15995, which contained pSRQ2201 (encoding for lactose utilization) and pSRQ2202 (encoding for the production of mucoid coagulum in milk cultures) was mated with non-mucoid, lactose-negative *Streptococcus lactis* ML-3/2.2 (as set forth in Ser. No. 786,631 now U.S. Pat. No. 4,918,014). As a result of the mating, a lactose-fermenting mucoid S. lactis transconjugant designated as S. lactis ML-3/2.230 was obtained. Plasmid-profile of a purified clone of S. lactis 5 ML-3/2.230 was compared with plasmid DNA derived from S. cremoris NRRL-B-15995. Although transconjugant S. lactis ML-3/2.230 was Lac+ (lactose-positive) and Muc+ (mucoid), corresponding plasmids pSRQ2201 and pSRQ2202 found in the S. cremoris donor were absent in the transconjugant S. lactis ML-3/2.230 contained two new plasmids, designated pSRQ2203 and pSRQ2204 which were not found in either the donor S. cremoris NRRL-B-15995 or the recipient S. lactis ML-3/2.2 (Table 3, and FIG. 4).

To determine which of the two plasmids namely, pSRQ2203 and pSRQ2204 coded for Muc+ phenotype in transconjugant S. lactis ML-3/2 230, plasmid curing experiments using high temperature incubation at 41° C. were made. Non-mucoid cured isolates were examined for plasmid DNA content. Non-mucoid, cured isolates with differing plasmid-profiles were obtained (Table 1, FIG. 1). The absence of either pSRQ2203 or pSRQ2204 resulted in the loss of mucoid characteristic. The loss of pSRQ2203 alone resulted in the loss of lactose-fermenting ability as well as the formation of mucoid coagulum In a separate curing experiment, transconjugant S. lactis ML-3/2.230 was consecutively transferred several times in whey-glucose broth and plated on BMLA as set forth in Ser. No. 786,631 now U.S. Pat. No. 4,918,014. Several lactose-negative colonies were examined for mucoidness in FNFM. One colony which was lactose-negative retained Muc+ phenotype. Plasmid profile of this isolate, S. lactis ML-3/2.233 showed that the isolate had pSRQ2204 intact but instead of pSRQ2203, a smaller plasmid, pSRQ2205 which represented a deleted species of pSRQ2203 was present (Table 3, FIG. 4). The deleted portion probably contained genetic information that was necessary for the expression of Lac+ phenotype The loss of pSRQ2205 by curing resulted in inability of S. lactis ML-3/2.233 to form mucoid coagulum in FNFM.

The inability of cured isolates lacking any one of the pair of plasmids (pSRQ2203 and pSRQ2204 or pSRQ2205 and pSRQ2204) to form a mucoid coagulum indicated that both plasmid elements were necessary for the expression of Muc+ phenotypes and each member of the pair carried partial genetic information for Muc+ phenotype. Plasmids pSRQ2203 and pSRQ2204 could have been formed by recombination of pSRQ2201 and pSRQ2202 during conjugal transfer.

EXAMPLE 2

To show pSRQ2203, pSRQ2204 and pSRQ2205 contained partial information found in pSRQ2202 for the phenotypic expression for mucoidness, purified pSRQ2202 DNA obtained from a derivative of S. lactis malty 4/4.201 as set forth in Ser. No. 786,631, now U.S. Pat. No. 4,918,014, was used as a probe to detect homology between pSRQ2202 and pSRQ2203, pSRQ2204 and pSRQ2205.

Plasmid DNA from malty 4/4.201, S. lactis ML-3/2.230, S. lactis ML-3/2.232, S. lactis ML-3/2.234, purified pSRQ2202 and S. lactis ML-3/2.233 were separated by agarose gel electrophoresis and transferred to nitrocellulose filter according to the procedure of Southern. Purified pSRQ2202 was used to prepare radiolabelled DNA hybridization probe by nick translation according to procedure recommended by New England Nuclear Corp., Boston, Mass. The radiolabelled pSRQ2202 probe was used in hybridization experiments on nitrocellulose filters according to procedures described by Silhavy et al. Washed and dried filters were autoradiographed with Kodak X-Omat film and Lightning-Plus screens (E. I. DuPont de Nemours & Co , Inc., Wilmington, Del.) at −70° C.

Autoradiographs showed hybridization between the pSRQ2202 probe and plasmids pSRQ2203, pSRQ2204 and pSRQ2205. Hybridization between the probe and pSRQ2201 and pSRQ2202 in S. lactis malty 4/4.201 was also observed. The hybridization found between the pSRQ2202 probe and the Lac-plasmid pSRQ2201 indicated that recombinational events between the plasmids pSRQ22101 and pSRQ2202 is possible. This substantiates the curing data showing that the genetic information for mucoidness is distributed between two separate plasmids in S. lactis ML-3/2.230 and S. lactis ML-3/2 233. Also a portion of pSRQ2203 encoded for Lac+ phenotype.

No hybridization occurred between the probe and any of the other resident plasmids in the strains included in the experiment. This indicated that the probe was quite specific.

EXAMPLE 3

To confirm the differences between mucoid and non-mucoid cultures in terms of the milk coagulum produced by the strains, viscosity measurements of mucoid and non-mucoid cultures were made with FNFM-grown cultures with the Boekel Viscosimeter (Zahn Cup type) according to the operating instructions of the manufacturer, Boekel Industries, Inc., Philadelphia, Pa. Mucoid strains showed at least two-fold greater viscosity than non-mucoid strains (Table 1, Footnotes).

It is intended that the foregoing description be only illustrative of the present invention and that the present invention be limited only by the hereinafter appended claims.

I claim:

1. *Streptococcus lactis* containing two plasmids derived form a single plasmid in *Streptococcus cremoris* NRRL-B-15995 as a result of conjugal transfer to the *Streptococcus lactis* which plasmids contain genes which are necessary to encode for mucoidness.

2. *Streptococcus lactis* NRRL-B-18337 (ML-3/2.230; pSRQ2203 and pSRQ2204).

3. *Streptococcus lactis* NRRL-B-18338 (ML-3/2.233; pSRQ2204 and pSRQ2205).

4. A *Streptococcus lactis* containing plasmids pSRQ2203 and pSRQ2204 as carried by NRRL-B-18337 (ML-3/2.230) both plasmids together encoding for the production of mucoidness.

5. A *Streptococcus lactis* containing plasmid pSRQ2204 and a plasmid partially encoding for mucoidness derived from a DNA deletion from pSRQ2203 wherein the plasmids pSRQ2203 and 2204 are carried by *Streptococcus lactis* NRRL-B-18337 (ML-3/2.230).

6. The *Streptococcus lactis* of claim 5 wherein the *Streptococcus lactis* is NRRL-B-18338 (ML-3/2.233).

7. A method for producing a *Streptococcus lactis* containing at least two plasmids which together contain genes which encode for mucoidness which comprises:
   (a) conjugating a *Streptococcus lactis* which does not produce mucoidness with a *Streptococcus cremoris* with DNA as contained in plasmid pSRQ2202 which contains a first plasmid encoding for mucoidness; and
   (b) isolating a strain containing two recombinant plasmids both of which contain the genes which are necessary to encode for mucoidness.

8. The method of claim 7 wherein the two plasmids were derived from pSRQ2202 as carried in *Streptococcus cremoris* NRRL-B-15995.

9. The method of claim 7 wherein the two recombinant plasmids are pSRQ2203 and pSRQ2204 as carried in *Streptococcus lactis* NRRL-B-18337.

10. The method of claim 7 wherein in addition the strain containing the two recombinant plasmids on spontaneous curing yields a *Streptococcus lactis* which deletes parts of one of the plasmids while retaining mucoidness.

11. The method of claim 10 wherein the strain is *Streptococcus lactis* carrying plasmids pSRQ2204 and pSRQ2205.

* * * * *

UNITED STATES PATENT AND TRADEMARK OFFICE
CERTIFICATE OF CORRECTION

PATENT NO. : 5,066,588

DATED : November 19, 1991

INVENTOR(S) : Ebenezer R. Vedamuthu

It is certified that error appears in the above—identified patent and that said Letters Patent is hereby corrected as shown below:

Title page, column 2, line 13, "Ezperiments" should be --Experiments--.

Column 2, line 1, "Sozziet al." should read --Sozzi et al.--.

Column 3, line 22, "1015 cells" should read --$10^{15}$ cells--.

Columns 3 and 4, Table 1, line 9, "ML-3.2.30" should read --ML-3/2.230--.
  and line 23 "ML-3.2.236" should read --ML-3/2.236--.

Columns 3 and 4, Table 1, line 9, "*S. cremoris* MS +" should read --*S. cremoris* MS X--.

Column 5, line 44, "ML-3/22" should read --ML-3/2.2--.

Column 5, line 47, "3/2202" should read --3/2.202--.

Column 5, line 49, ML-3/2 230" should read --ML-3/2.230--.

Column 5, line 51, after "pSRQ2202" and before "Instead", a period --.-- should be inserted.

Column 5, line 64, "strains" should be --strain--.

Column 6, line 34, after "High", the comma "," should be deleted.

UNITED STATES PATENT AND TRADEMARK OFFICE
CERTIFICATE OF CORRECTION

PATENT NO. : 5,066,588

DATED : November 19, 1991

INVENTOR(S) : Ebenezer R. Vedamuthu

It is certified that error appears in the above—identified patent and that said Letters Patent is hereby corrected as shown below:

Column 6, line 56, "ML-3/2233" should read --ML-3/2.233--.

Column 7, line 16, after "transfer" a period --.-- should be inserted.

Column 7, line 20, "ML-3/2" should read --ML-3/2.--.

Column 7, line 47, "S. lactis 5 ML-3" should read --S. lactis ML-3--.

Column 7, line 60, "ML-3/2 230" should read --ML-3/2.230--.

Column 7, line 68, after "coagulum" a period --.-- should be inserted.

Column 8, line 14, after "phenotype" and before "The", a period --.-- should be inserted.

UNITED STATES PATENT AND TRADEMARK OFFICE
CERTIFICATE OF CORRECTION

PATENT NO. : 5,066,588

DATED : November 19, 1991

INVENTOR(S) : Ebenezer R. Vedamuthu

It is certified that error appears in the above—identified patent and that said Letters Patent is hereby corrected as shown below:

Column 8, line 59, "pSRQ22101" should read --pSRQ2201--.

Column 8, line 62, "ML-3/2 233" should read --ML-3/2.233--.

Column 9, line 18 (Claim 1), "form" should be --from--.

Signed and Sealed this

Sixteenth Day of November, 1993

BRUCE LEHMAN

*Attest:*

*Attesting Officer*    Commissioner of Patents and Trademarks